United States Patent
Bezicot et al.

(10) Patent No.: US 6,186,139 B1
(45) Date of Patent: Feb. 13, 2001

(54) DISPOSABLE RESPIRATORY FILTER FOR TRACHEOTOMIZED SUBJECT

(76) Inventors: Robert Bezicot, 48 rue Joseph Fouriaux; Eric Bezicot, 35 Avenue du 11 Novembre; Daniele Voranger, 48 rue Joseph Fouriaux, all of 92160 Antony (FR)

(*) Notice: Under 35 U.S.C. 154(b), the term of this patent shall be extended for 0 days.

(21) Appl. No.: 09/214,289

(22) PCT Filed: Jul. 1, 1997

(86) PCT No.: PCT/FR97/01170
§ 371 Date: Mar. 1, 1999
§ 102(e) Date: Mar. 1, 1999

(87) PCT Pub. No.: WO98/00189
PCT Pub. Date: Jan. 8, 1998

(30) Foreign Application Priority Data

Jul. 1, 1996 (FR) .................................................. 96 08171

(51) Int. Cl.[7] .................................................. A61M 15/00
(52) U.S. Cl. .............................. 128/200.24; 128/207.17; 128/918
(58) Field of Search ................ 128/200.24, 207.17, 128/888, 909, 918, DIG. 26

(56) References Cited

U.S. PATENT DOCUMENTS

| | | | |
|---|---|---|---|
| 2,900,640 | * 8/1959 | Haydu | 2/49.1 |
| 3,286,713 | * 11/1966 | Kurtz et al. | 128/DIG. 26 |
| 3,422,817 | * 1/1969 | Mishkin et al. | 128/DIG. 26 |
| 3,811,436 | * 5/1974 | Ferrell | 128/207.17 |
| 3,824,999 | * 7/1974 | King | 128/207.17 |
| 4,622,698 | 11/1986 | Heyman et al. | 2/49.1 |
| 4,787,099 | * 11/1988 | Mack | 2/49.1 |
| 4,862,518 | * 9/1989 | Williams et al. | 2/49.1 |
| 4,891,846 | * 1/1990 | Sager et al. | 2/49.1 |
| 5,181,274 | * 1/1993 | Defiore | 128/888 |
| 5,306,233 | 4/1994 | Glover | 602/41 |
| 5,616,116 | * 4/1997 | Born | 128/207.17 |
| 5,875,490 | * 3/1999 | Woodard et al. | 2/49.1 |
| 6,000,056 | * 12/1999 | Brady et al. | 2/49.1 |

FOREIGN PATENT DOCUMENTS

| | | |
|---|---|---|
| 35 25 658 | 2/1986 | (DE) . |
| 0 370 962 | 5/1990 | (EP) . |
| 2 202 823 | 10/1988 | (GB) . |

* cited by examiner

Primary Examiner—Aaron J. Lewis
(74) Attorney, Agent, or Firm—Young & Thompson

(57) ABSTRACT

A filter for covering a surgical orifice at a base of the neck of a tracheotomized person and connecting the trachea to the ambient atmosphere. The filter comprises a bib having a cutout neck with a border extended by one or more attachment strips adapted to form with the border a closed loop around the neck of the person by complementary joining elements which may not be separated after being joined, so that the filter cannot be re-used.

10 Claims, 1 Drawing Sheet

DISPOSABLE RESPIRATORY FILTER FOR TRACHEOTOMIZED SUBJECT

CROSS REFERENCE TO RELATED APPLICATION

This is the national stage of international application PCT/FR97/01170, filed on Jul. 1, 1997, which designated the USA.

BACKGROUND OF THE INVENTION

The invention concerns a filter to be placed over the surgical orifice at the base of the neck connecting the trachea of a tracheotemized person to the outside, the filter comprising a filter material bib with a cut-out neck and a border extended by at least an attachment strip adapted to form with the border a closed loop around the neck of the person by joining together of complementary joining means.

A surgical orifice at the base of the neck and connecting the trachea directly to the outside enabling the person to breathe in and out unaided is made during surgery to the upper respiratory tract, above the trachea, for example for sarcoma of the larynx.

Breathing in and out does not then benefit from the filtering, warming and saturation with water vapor functions effected by the passage of air breathed in via the nostrils, the nasal fossae and the pharynx.

DESCRIPTION OF RELATED PRIOR ART

To compensate for the elimination of these functions, "artificial noses" have been proposed in which the presence of a hygroscopic spongy mass in the breathed air path provides the three-fold function of filtering, warming and saturation with water vapor, the latter two functions condensing moisture in the air leaving the lungs on breathing out and evaporating moisture retained by the spongy mass on breathing in, together with corresponding heat exchanges. A "nose" of this kind is described in patent document FR-A-2 683 150, for example.

Because of the inherent weight of an artificial nose and because of the contact of the material of the nose with the tissues, some persons find wearing an artificial nose of the above kind somewhat uncomfortable. Also, the fitting of an artificial nose is undesirable during the post-operative period, before complete healing of the scars and stabilization of the surgical orifice.

Provided that certain precautions are taken with regard to the environment, temperature and relative humidity, it is possible to attenuate the drawbacks of direct entry into the trachea of air with uncontrolled temperature and relative humidity. However, the filter function is still necessary, not to say essential, unless the person is kept under clean room conditions. The necessary filtering involves preventing the entry of relatively large foreign bodies, such as parts of clothing.

In the early post-operative period the filtering function is assured by dressings arranged appropriately to enable air to pass through whilst protecting the exposed tissues. Such dressings are merely temporary, however. The devices taking the place of these dedicated dressings must be light in weight, easy to fit, effective as filters and in their role of protecting against entry of foreign bodies, and sufficiently sterile.

Filters in the form of bibs are available off the shelf, comprising a material formed of multiple thicknesses of filter fabric with a cut-out neck, the border of which is extended by two attachment straps that attach to each other to form a closed loop around the person's neck so that the bib hangs down onto the front of the person's torso, covering the surgical orifice leading to the trachea. The multiple thicknesses of fabric assure efficient filtering with a fabric that is loose enough to provide sufficient permeability to air. The diameter of the threads of the fabric cannot be made infinitely small and so the permeability of a fabric, depending on the surface area between the threads and the total surface area, requires passages of large unit surface area, with the result that it is necessary to stack several thicknesses of fabric to obtain sufficient blocking of fine particles. The fabric is washable.

Clearly the efficacy of the expected filtering result presupposes that the bib filter is changed frequently and washed regularly and carefully. Also, the cost of such filters is by no means negligible, given their construction, which entails a large number of manufacturing operations, and the stock required for regular changing. Also, regular changing and washing may be compromised inadvertently or because of negligence, leading to serious risks.

Document DE 3 525 658 describes a neck cover designed to protect access to the surgical opening of persons who have undergone surgery of the larynx and comprising a piece of loosely woven tissue (so that air can pass through it) hanging in front of the surgical opening with a shape corresponding to a V-shaped neck of an open-neck shirt or pullover and fixed to the neck of the person by a sewn strip, the ends of which are joined by "textile" closure pieces (i.e. of the "Velcro" type). The fabric is advantageously lined on the side towards the neck with thicknesses of tulle. The neck cover of the above document has, without prejudice to advantages and disadvantages compared to the bib described previously, the same disadvantages as that bib associated with reuse, namely the need for it to be maintained in a sterile condition and the risks of non-sterility resulting from failure to wash it or imperfect washing.

BRIEF SUMMARY OF THE INVENTION

To alleviate the above drawbacks, the invention proposes a filter adapted to cover a surgical orifice at the base of the neck connecting the trachea of a tracheotemized person to the outside, the filter comprising a filter material bib having a cut-out neck with a border extended by at least one attachment strip adapted to form, with said border, a closed loop around the neck of the person by joining together of complementary joining means, characterized in that the joining means, once joined, cannot be separated without rendering them unserviceable, with the result that the filter cannot be reused.

The inventors are aware that the hygiene required can be attained only if the filter, which is sterile when new, cannot be reused and must be discarded after a single use. This implies, firstly, that the unit cost should be low (materials and manufacturing process) so that the person is not tempted to reuse it, and, secondly and more importantly, that the filter is not able to be reused after a single use. The latter result is achieved by employing joining means that work only once, so that after the bib has been removed it is no longer possible to fix it around the person's neck again. Note that the two results referred to, namely low cost and difficult re-use, combine to dissuade the person from attempting to re-use the filter. Note also that single-use items such as paper handkerchiefs are in practice rendered unusable by the first use made of them whereas respiratory filters cannot indicate that their first use has made them inadequate in terms of protection.

The filter material is preferably a non-woven film which combines the advantages of low cost, easy manufacture by cutting out on a press, the ability to adjust its porosity with pores that are small by their very nature, and limited intrinsic cohesion, favoring the rendering of the joining means unserviceable after they are separated.

In a preferred arrangement, the bib has on a face designed to come into contact with the torso of the person an adhesive area in the form of an adhesive strip disposed substantially transversely to the bottom of the neck. This adhesive area is fixed to the neck of the subject, above the surgical orifice. It then assures that the filter material is kept spread across the front of the surgical orifice despite movements of the person and rubbing of their clothing. Also, the at least partial ablation of the larynx resulting from the tracheotomy produces a depression at the base of the neck around the surgical opening. Holding the filter material onto the neck above the surgical orifice prevents a space forming between the bib and the neck through which non-filtered air could pass.

Also, the bib preferably has, as far as possible from the neck, two adhesive areas adapted to hold the bottom part of the bib against the skin to perfect the spreading of the bib over the torso.

It is also desirable for the bib to have in the middle a rib extending radially to the neck with its end near the neck such that it bridges the surgical orifice. This is to prevent obstruction of the surgical orifice due to the effect of the breath.

The filter is supplied to the person sterile, enclosed in a sealed sachet.

BRIEF DESCRIPTION OF THE DRAWINGS

Secondary features and advantages of the invention will emerge from the following description which is given by way of example and with reference to the accompanying drawings.

DETAILED DESCRIPTION OF THE INVENTION

In the selected embodiment of the invention shown in the figures, a respiratory filter 1 for a tracheotemized person is in the form of an unwoven film cut to the shape of a bib with a cut-out neck 2 the border of which is extended by attachment strips 3 and 3' which are straight and in one piece with the remainder of the bib.

Figure 1:
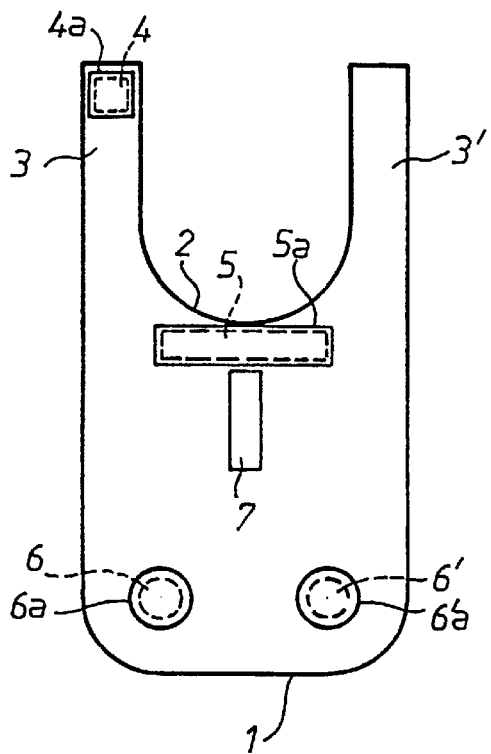
FIG. 1 shows a filter in accordance with the invention, seen from behind.
Figure 2:
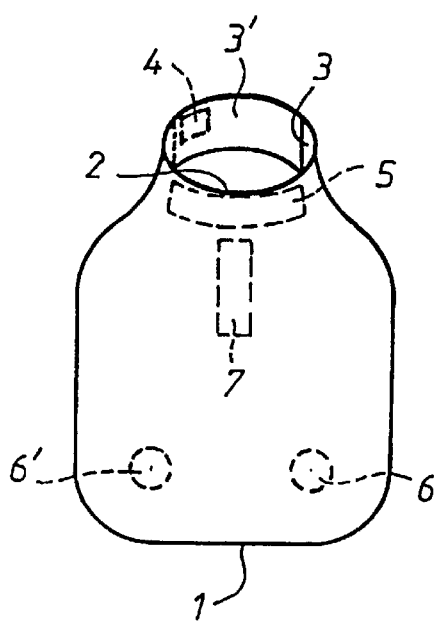
FIG. 2 shows the filter from FIG. 1, in place, with the attachment strips joined together.
Figure 3:
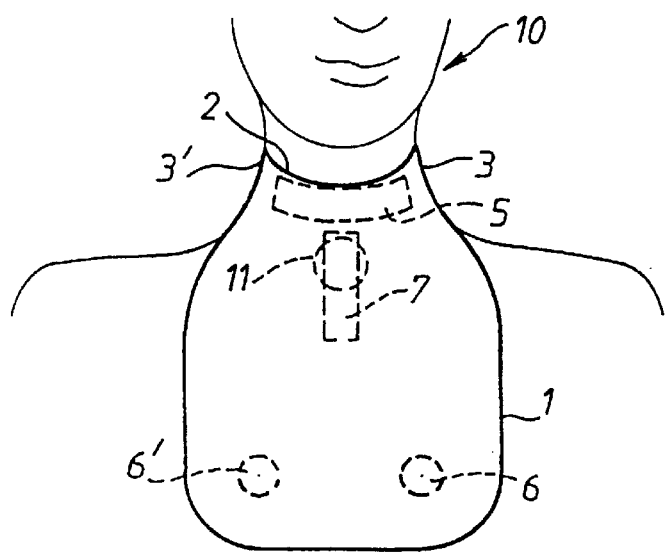
FIG. 3 shows a person wearing the filter.

On the face of the film constituting the bib 1 that is to come into contact with the torso of the person, referred to herein as the rear face and that shown in FIG. 1, the strip 3 (on the left in FIG. 1) has at the end a pad 4 of pressure-sensitive adhesive covered in the usual way with a protective film 4a. As shown in FIG. 2, by cooperation with the front face of the attachment strip 3', the adhesive pad 4 forms with the border of the neck 2 a closed loop around the neck of the person, as shown in FIG. 3. The adhesive pad 4 on the strip 3 and the front face of the strip 3' constitute complementary joining means. The adhesive of the pad 4 has a consistency such that the join is resistant to traction forces resulting from movements of the person and also such that subsequent separation of the strips 3 and 3' makes it impossible to rejoin them, either because one of the strips tears or because the outside face of the adhesive retains non-woven debris torn away from the front face of the strip 3' and no longer has any sticking power.

The rear face of the bib 1 has, symmetrical about its middle in the radial direction of the neck cut-out (which assumes a vertical direction when the filter is worn by a person as shown in FIG. 3), an adhesive area 5 in the form of a strip disposed substantially transversely to the bottom of the neck cut-out and covered with a protective film 5a. Further away from the neck cut-out the rear face of the bib carries two adhesive pads 6, 6' symmetrical about its center. The pads 6, 6' are covered with protective films 6a, 6'a.

A rib 7 is stuck to the rear face of the bib, oriented along its middle, with one end near the neck cut-out substantially level with the bottom of the adhesive pad 5. These features and their functions will be described in more detail below.

Note, however, that the adhesive used for the pads 5, 6, 6' must be physiologically compatible with the skin while that of the pad 4 does not necessarily have to satisfy this condition. However, it is possible to choose an adhesive that meets both conditions.

The rib 7 is a strip of a semi-rigid polymer material that can adapt to the curvature of the sternum but offers adequate resistance to crumpling.

As shown in FIGS. 2 and 3, to join together the two attachment strips, the strip 3' is passed over the right shoulder of a person 10 (of whom only the outline of the neck, chin and shoulders have been sketched in), after which the strip 3, passed over the left shoulder, is pressed onto the strip 3' so that the adhesive pad 4 sticks to the strip 3' (rear face), forming a close fit around the neck of the person 10.

As shown in FIG. 3, the tracheotemized person 10 has a surgical orifice 11 at the base of their neck that connects the trachea to the outside. The bib is positioned so that its middle portion is in front of the surgical orifice and the pad 5 is symmetrical about the orifice and above it. The location of the rib 7 on the bib 1 is such that it bridges the surgical orifice 11. The stiffness of the rib 7 and the adhesion of the adhesive pad 5 assure that the bib covers the surgical orifice, taking up a position in front of it, without entering the orifice or allowing air to pass directly to the orifice without passing through the non-woven material or forming folds that would produce stacked thicknesses of the filter material increasing head losses in the filter.

The pads 6, 6' cooperate to hold the bib 1 in position on the person 10, preventing the bottom of the bib rising up because of movement of the person in conjunction with the rubbing of clothing placed on top of it.

The filter bibs are made available to tracheotemized persons after sterilization by an appropriate process and packaging of each filter in a sealed sachet.

The adhesive pad 4 could be on either of the attachment strips 3, 3' and equally well on the front face as on the rear face, although placing it on the rear face has the advantage of enabling the adhesive of the pads 4, 5, 6, 6' to be applied in a single operation.

What is claimed is:

1. Filter adapted to cover a surgical orifice (11) at the base of the neck connecting the trachea of a tracheotemized person (10) to the outside, the filter comprising a filter material bib (1) having a cut-out neck (2) with a border extended by at least one attachment strip (3, 3') adapted to form, with said border, a closed loop around the neck of the person (10) by joining together of complementary joining means (4, 3'), characterized in that the joining means (4, 3') are such that, once joined, separating them opens said loop in an irreversible manner, with the result that the filter cannot be reused.

2. Filter according to claim 1 characterized in that the filter material is a non-woven film.

3. Filter according to claim 1 characterized in that it includes two attachment strips (3, 3'), the joining means (4, 3') being on both attachment strips.

4. Filter according to claim 3 characterized in that the attachment strips (3, 3') are in one piece with the bib (1).

5. Filter according to claim 1 characterized in that at least one of the joining means (4) is a single use pressure-sensitive adhesive layer.

6. Filter according to claim 1 characterized in that the bib has on a face intended to come into contact with the torso of the person an adhesive pad (5) in the form of a strip disposed transversely substantially at the bottom of the cut-out neck (2).

7. Filter according to claim 6 characterized in that the bib includes, at the greatest possible distance from the cut-out neck (2), two adhesive pads (6, 6') adapted to hold the bottom part of the bib (1) against the skin of the torso of the person.

8. Filter according to claim 7 characterized in that the bib (1) has a rib (7) in the middle extended radially relative to the cut-out neck (2) with an end near the latter which bridges the surgical orifice (11).

9. Filter according to claim 6 characterized in that the bib (1) has a rib (7) in the middle extended radially relative to the cut-out neck (2) with an end near the latter which bridges the surgical orifice (11).

10. Filter according to claim 1 characterized in that it is supplied to the person (10) in a sterile state packaged in a sealed sachet.

* * * * *